United States Patent [19]

Peter et al.

[11] 4,014,874

[45] Mar. 29, 1977

[54] PROCESS FOR THE MANUFACTURE OF 3-SUBSTITUTED THIOMETHYL-7-AMINO-2-CEPHEM-4-CARBOXYLIC ACID COMPOUND

[75] Inventors: Heinrich Peter, Binningen; Beat Müller, Reinach, both of Switzerland; Walter Sibral, Tulln, Austria; Hans Bickel, Binningen, Switzerland

[73] Assignee: Ciba-Geigy Corporation, Ardsley, N.Y.

[22] Filed: Jan. 27, 1975

[21] Appl. No.: 544,442

[30] Foreign Application Priority Data

Feb. 5, 1974  Switzerland .................. 1555/74

[52] U.S. Cl. ........................................ 260/243 C
[51] Int. Cl.$^2$ ..................................... C07D 501/06
[58] Field of Search ............................ 260/242 C

[56] References Cited

UNITED STATES PATENTS

| | | | |
|---|---|---|---|
| 3,867,380 | 2/1975 | Dunn et al. | 260/243 C |
| 3,878,204 | 4/1975 | Ochiai et al. | 260/243 C |
| 3,891,629 | 6/1975 | Diassi et al. | 260/243 C |
| 3,948,905 | 4/1976 | De Marinis et al. | 260/243 C |
| 3,965,099 | 6/1976 | De Marinis et al. | 260/243 C |
| 3,975,385 | 8/1976 | Bouchaudon et al. | 260/243 C |

*Primary Examiner*—Nicholas S. Rizzo
*Assistant Examiner*—David E. Wheeler
*Attorney, Agent, or Firm*—Joseph G. Kolodny; John J. Maitner; Theodore O. Groeger

[57] ABSTRACT

The invention concerns a new process for the manufacture of 3-substituted thiomethyl-7-amino-3-cephem-4-carboxylic acid compounds which comprises reacting a 3-y-methyl-7-amino-3-cephem-4-carboxylic acid compound, in which Y is hydroxy or esterified hydroxy, with a mercaptane compound, if necessary, in the presence of an optionally protonic Lewis acid, particularly trifluoroacetic acid.

5 Claims, No Drawings

PROCESS FOR THE MANUFACTURE OF 3-SUBSTITUTED THIOMETHYL-7-AMINO-2-CEPHEM-4-CARBOXYLIC ACID COMPOUND

The present invention relates to a new process for the manufacture of 7-N-$R_1^a$-N-$R_1^b$-amino-3R-thio-methyl-2-cephem-4ξ-carboxylic acid compounds of the formula

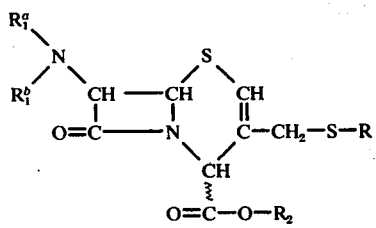

wherein R denotes a lower aliphatic hydrocarbon radical or a heretocyclic radical, bonded to the sulphur via a ring carbon atom, which contains 1 to 4 ring nitrogen atoms and optionally a further ring hetero-atom from the group of oxygen and sulphur, $R_1^a$ represents hydrogen or an amino protective group $R_1^A$ and $R_1^b$ represents hydrogen or an acyl group Ac, or $R_1^a$ and $R_1^b$ together denote a divalent amino protective group, and $R_2$ represents hydrogen or a radical $R_2^A$ which together with the —C(=O)—O— grouping forms a protected carboxyl group, or of salts of such compounds which have salt-forming groups.

A lower aliphatic hydrocarbon radical R is above all lower alkyl and especially methyl, as well as lower alkenyl or lower alkinyl.

A heretocyclic radical R defined as above is, for example, an optionally substituted, bicyclic, but preferably monocyclic, heterocyclic radical, which has aromatic properties or can be partially saturated.

An amino protective group $R_1^A$ is, for example, one of the generally known groups of this type, such as a triarylmethyl group, for example a trityl group, or an organic silyl group, such as a tri-lower alkylsilyl group, for example the trimethylsilyl group, or a corresponding organic stannyl group, or, above all, an acyl group Ac.

An acyl group Ac is above all the acyl radical of an optionally substituted aliphatic, cycloaliphatic cycloaliphatic-aliphatic, aromatic, aralipatic, heterocyclic or heterocyclic-aliphatic carboxylic acid (including formic acid), such as acyl radical preferably containing up to 20 carbon atoms, or the acyl radical of a carbonic acid half-derivative, such as a corresponding half-ester or half-amide.

A divalent amino protective group formed by the radicals $R_1^a$ and $R_1^b$ together is in particular the divalent acyl radical of an organic dicarboxylic acid, above all the diacyl radical of an aliphatic or aromatic dicarboxylic acid, or the acyl radical of an α-aminoacetic acid which is preferably substitued in the α-position, for example contains an aromatic or heterocyclic radical in the α-position, wherein the amino group is bonded to the nitrogen atom via a methylene radical which is preferably substituted, for example a methylene containing two lower alkyl groups, such as methyl groups. The radicals $R_1^a$ and $R_1^b$ can together also represent an organic ylidene radical, such as aliphatic, cycloaliphatic, cycloaliphatic-aliphatic or aralipatic ylidene radical.

A protected carboxyl group of the formula —(C=O)—O—$R_2^A$ is above all an esterified carboxyl group but can also be an anhydride group, usually a mixed anhydride group.

The group $R_2^A$ can represent an organic radical which together with the —C(=O)—O— grouping forms an esterified carboxyl group which can preferably be split easily; examples of such radicals are aliphatic, cycloaliphatic, cycloaliphatic-aliphatic, aromatic or aralipatic radicals, especially optionally substituted hydrocarbon radicals of this nature, as well as heterocyclic or heterocyclic-aliphatic radicals. The group $R_2^A$ can also represent an organic silyl radical, or an organo-metallic radical, such as a corresponding organic stanyl radical, especially a silyl or stannyl radical which is substituted by 1 to 3 optionally substituted hydrocarbon radicals, such as aliphatic hydrocarbon radicals, for example a di-lower alkyl-halogenosilyl or tri-lower alkyl-silyl or -stannyl group or a disubstituted, such as di-lower alkylated, silyl or stannyl group which substitutes two carboxyl groups —C(=O)—O—.

A radical $R_2^A$ which forms an anhydride group, preferably a mixed anhydride group, with the —C(=O)—O— grouping is preferably the acyl radical of an organic carboxylic acid, such as of an aliphatic, cycloaliphatic, cycloaliphatic-aliphatic, aromatic or aralipatic carboxylic acid, or of a carbonic acid half-derivative, such as a carbonic acid half-ester.

Examples of substituents in heterocyclic radicals R are lower alkyl, especially methyl, hydroxy-lower alkyl, for example hydroxymethyol, cycloalkyl, for example cyclopentyl or cyclohexyl, aryl, such as phenyl optionally substituted by halogen, for example chlorine, or nitro, aryl-lower alkyl, such as benzyl which is optionally substituted, for example like a phenyl radical, or heterocyclyl, such as furyl, thienyl or oxazolyl, or functional groups, such as halogen, optionally substituted amino, such as amino optionally monosubstituted or disubstituted by lower alkyl, nitro, lower alkoxy, or optionally functionally modified carboxyl, such as carboxyl, esterified carboxyl, such as lower alkoxycarbonxyl, optionally substituted, such as N-mono- or N,N-di-lower alkylated carbamoyl, or cyano, as well as oxo or oxido, it being possible for one or more such substituents to be present, the substituents above all being bonded to ring carbon atoms but also, especially in the case of lower alkyl and oxido, to ring nitrogen atoms.

Heterocyclic radicals R are above all monocyclic five-membered, diazacyclic, triazacyclic, tetrazacyclic, thiazacyclic, thiadiazacyclic, thiatriazacyclic, oxazacyclic or oxadiazacyclic radicals of aromatic character which are optionally substituted, for example which contain the abovementioned substituents, especially lower alkyl, for example methyl, or corresponding radicals which are optionally substituted, for example contain the abovementioned substituents, and have a fused-on benzene ring, such as benzodiazacyclic and benzooxazacyclic radicals, monocyclic, six-membered monoazacyclic or diazacyclic radicals of aromatic character which are optionally substituted, for example which contain the abovementioned substituents, above all oxido, or corresponding partially saturated radicals which are optionally substituted, for example which contain the abovementioned substituents, above all oxo, or bicyclic triazacyclic or tetrazacyclic radicals of aromatic character which are optionally substituted, for example which contain the abovementioned substituents, or corresponding partially saturated radicals which are optionally substituted, for example which contain the abovementioned substituents, above all oxo.

Preferred monocyclic, five-membered heterocyclic radicals R or corresponding benzoheterocyclic radicals R are inter alia, imidazolyl, for example 2-imidazolyl, triazolyl which is optionally substituted by lower alkyl and/or phenyl, for example s-triazol-2-yl, 5-methyl-s-triazol-2-yl, 1H-1,2,4-triazol-5-yl, 3-methyl-1-phenyl-1H-1,2,4-triazol-5-yl, 4,5-dimethyl-4H-1,2,4-triazol-3-yl or 4-phenyl-4H-1,2,4-triazol-3-yl, tetrazolyl which is optionally substituted by lower alkyl, phenyl or halogenophenyl, for example 1H-5-tetrazolyl, 1-methyl-1H-5-tetrazolyl, 1-phenyl-1H-5-tetrazolyl or 1-(4-chlorophenyl)-1H-5-tetrazolyl, thiazolyl which is optionally substituted by lower alkyl or thienyl, for example 2-thiazolyl, 4-(2-thienyl)-2-thiazolyl or 4,5-dimethyl-2-thiazolyl, thiadiazolyl which is optionally substituted by lower alkyl, for example 1,3,4-thiadiazol-2-yl, 2-methyl-1,3,4-thiadiazol-5-yl or 1,2,4-thiadiazol-5-yl, thiatriazolyl, for example 1,2,3,4-thiatriazolyl-5-yl, oxazolyl or isoxazolyl which is optionally substituted by lower alkyl or phenyl, for example 5-oxazolyl, 4-methyl-5-oxazolyl, 2-oxazolyl, 4,5-diphenyl-2-oxazolyl or 3-methyl-5-isoxazolyl, oxadiazolyl which is optionally substituted by lower alkyl, phenyl, nitrophenyl or thienyl, for example 1,2,4-oxadiazol-5-yl, 2-methyl-1,3,4-oxadiazol-5-yl, 2-phenyl-1,3,4-oxadiazol-5-yl, 5-(4-nitrophenyl)-1,3,4-oxadiazol-2-yl or 2-(thienyl)-1,3,4-oxadiazol-5-yl, benzimidazolyl which is optionally substituted by halogen, for example 2-benzimidazolyl or 5-chloro-2-benzimidazolyl, or benzoxazolyl which is optionally substituted by halogen or nitro, for example 2-benzoxazolyl, 5-nitro-2-benzoxazolyl or 5-chloro-2-benzoxazolyl.

Preferred monocyclic, six-membered heterocyclic radicals R or corresponding partially saturated radicals are, inter alia, 1-oxido-pyridyl which is optionally substituted by halogen, for example 1-oxido-2-pyridyl or 4-chloro-1-oxido-2-pyridyl, N-oxido-pyridazinyl which is optionally substituted by lower alkyl, lower alkoxy or halogen, for example 2-oxido-6-pyridazinyl, 3-chloro-1-oxido-6-pyridazinyl, 3-methyl-2-oxido-6-pyridazinyl, 3-methoxy-1-oxido-6-pyridazinyl, 3-ethoxy-1-oxido-6-pyridazinyl, 3-n-butoxy-1-oxido-6-pyridazinyl or 3-(2-ethylhexyloxy)-1-oxido-6-pyridazinyl, or 2-oxo-1,2-dihydro-pyrimidinyl which is optionally substituted by lower alkyl, amino, di-lower alkylamino or carboxyl, for example 2-oxo-1,2-dihydro-4-pyrimidinyl, 6-methyl-2-oxo-1,2-dihydro-4-pyrimidinyl, 5-methyl-2-oxo-1,2-dihydro-4-pyrimidinyl, 6-amino-2-oxo-1,2-dihydro-4-pyrimidinyl, 6-dimethylamino-2-oxo-1,2-dihydro-4-pyrimidinyl, 5-carboxy-2-oxo-1,2-dihydro-4-pyrimidinyl or 6-carboxy-2-oxo-1,2-dihydro-4-pyrimidinyl.

Preferred heterocyclic bicyclic optionally partially saturated radicals R are, inter alia, triazolopyridyl, for example 3-s-triazolo[4,3-a]pyridyl or 5-v-triazolo[4,5-b]pyridyl, or purinyl which is optionally substituted by halogen and/or lower alkyl, for example 2-purinyl, 6-purinyl or 8-chloro-2-methyl-6-purinyl, and also 2-oxo-1,2-dihydropurinyl, for example 2-oxo-1,2-dihydro-6-purinyl.

An acyl group Ac in particular represents an acyl radical of an organic carboxylic acid, or of a carbonic acid half-derivative, contained in a naturally occuring or bio-synthetically, semi-synthetically or entirely synthetically preparable, preferably pharmacologically active, N-acyl derivative of 6-amino-2,2-dimethyl-penam-3-carboxylic acid compounds or 7-amino-3-cephem-4-carboxylic acid compounds, especially of 6-aminopenicillanic acid or 7-amino-cephalosporanic acid, or represents an easily removable acyl radical, especially of a carbonic acid half-derivative.

An acyl radical Ac contained in pharmacologically active N-acyl derivatives of 6-amino-2,2-dimethyl-penam-3-carboxylic acid compounds or 7-amino-3-cephem-4-carboxylic acid compounds is above all a group of the formula

wherein $n$ represents 0 and $R^I$ represents hydrogen or an optionally substituted cycloaliphatic or aromatic hydrocarbon radical, or an optionally substituted heterocyclic radical, preferably of aromatic character, a functionally modified, preferably etherified, hydroxyl or mercapto group of an optionally substituted amino group, or wherein $n$ represents 1, $R^I$ represents hydrogen or an optionally substituted aliphatic, cycloaliphatic, cycloaliphatic-aliphatic, aromatic or araliphatic hydrocarbon radical or an optionally substituted heretocyclic or heterocyclic-aliphatic radical, wherein the heterocyclic radical preferably possesses aromatic character and/or possesses a quaternary nitrogen atom, an optionally functionally modified, preferably etherified or esterified, hydroxyl or mercapto group, an optionally functionally modified carboxyl group, an acyl group, an optionally substituted amino group or an azido group, and each of the radicals $R^{II}$ and $R^{III}$ denotes hydrogen, or wherein $n$ represents 1, $R^I$ denotes an optionally substitued aliphatic, cycloaliphatic, cycloaliphatic-aliphatic, aromatic or araliphatic hydrocarbon radical or an optionally substituted heretocyclic or heterocyclic-aliphatic radical, wherein the heterocyclic radical preferably has aromatic character, $R^{II}$ denotes an optionally functionally modified, preferably etherified, hydroxyl or mercapto group, an optionally substituted amino group, an optionally functionally modified carboxyl or sulpho group, an azido group or a halogen atom, and $R^{III}$ represents hydrogen, or wherein $n$ represents 1, each of the radicals $R^I$ and $R^{II}$ denotes a functionally modified, preferably etherified or esterified, hydroxyl group or an optionally functionally modified carboxyl group, and $R^{III}$ represents hydrogen, or wherein $n$ represents 1, $R^I$ denotes hydrogen or an optionally substituted aliphatic, cycloaliphatic-aliphatic, aromatic or araliphatic hydrocarbon radical, and $R^{II}$ and $R^{III}$ together represent an optionally substituted aliphatic, cycloaliphatic, cycloaliphatic-aliphatic or araliphatic hydrocarbon radical which is bonded to the carbon atom by a double bond, or wherein $n$ represents 1 and $R^I$ denotes an optionally substituted aliphatic, cycloaliphatic, cycloaliphatic-aliphatic, aromatic or araliphatic hydrocarbon radical or an optionally substituted heterocyclic or heterocyclic-aliphatic radical, wherein heterocyclic radicals preferably possess aromatic character, $R^{II}$ denotes an optionally substituted aliphatic, cycloaliphatic, cycloaliphatic-aliphatic, aromatic or araliphatic hydrocarbon radical and $R^{III}$ denotes hydrogen or an optionally substituted aliphatic, cycloaliphatic, cycloaliphatic-aliphatic, aromatic or araliphatic hydrocarbon radical.

In the abovementioned acyl groups of the formula Ia, for example, n represents 0 and $R^I$ represents hydrogen or a cycloalkyl group with 5–7 ring carbon atoms which is optionally substituted, preferably in the 1-position, by optionally substituted amino, such as amino, acylamino, wherein acyl above all represents the acyl radical of a carbonic acid half-ester, such as a lower alkoxycarbonyl, 2-halogen-lower alkoxycarbonyl or phenyl-lower alkoxycarbonyl radical, or a sulphoamino group which is optionally present in the form of a salt, for example in the form of an alkali metal salt, a phenyl, naphthyl or tetrahydronaphthyl group which is optionally substituted, preferably by hydroxyl, lower alkoxy, for example methoxy, acyloxy, wherein acyl above all represents the acyl radical of a carbonic acid half-ester, such as a lower alkoxycarbonyl, 2-halogen-lower alkoxycarbonyl or phenyl-lower alkoxycarbonyl radical, and/or halogen, for example chlorine, a heterocyclic group, which is optionally substituted, for example by lower alkyl, for example methyl, and/or phenyl, which can in turn carry substituents, such as halogen, for example chlorine, such as a 4-isoxazolyl group, or an amino group which is preferably N-substituted, for example by an optionally substituted lower alkyl radical, such as a lower alkyl radical containing halogen, for example chlorine, or n represents 1, $R^I$ represents a lower alkyl group which is optionally substituted, preferably by halogen, such as chlorine, by phenyloxy which is optionally substituted, such as phenyloxy containing hydroxyl, acyloxy, wherein acyl has the abovementioned meaning, and/or halogen, for example chlorine, or by optionally protected amino and/or carboxyl, for example represents a 3-amino-3-carboxy-propyl radical which has an optionally protected amino and/or carboxyl group, for example a silylated, such as a tri-lower alkylsilylated, for example trimethylsilylated, amino or acylamino, such as lower alkanoylamino, halogeno-lower alkanoylamino or phthaloylamino group, and/or a silylated, such as tri-lower alkylsilylated, for example trimethylsilylated, carboxyl group, or an esterified carboxyl group, such as a carboxyl group esterified by lower alkyl, 2halogeno-lower alkyl or phenyl-lower alkyl, for example diphenylmethyl, or represents a lower alkenyl group, or represents a phenyl group which is optionally substituted, such as a phenyl group which contains hydroxyl which is optionally acylated, for example as indicated above, and/or halogen, for example chlorine, annd also amino-lower alkyl, such as aminomethyl, which is optionally protected, for example acylated as indicated above, or phenyloxy which is optionally substituted, such as phenyloxy which contains hydroxyl which is optionally acylated, for example as indicated above, and/or halogen, for example chlorine, or represents a pyridyl group, for example 4-pyridyl group, pyridinium group, for example 4-pyridinium group, thienyl group, for example 2-thienyl group, furyl group, for example 2-furyl group, imidazoyl group, for example 1imidazoyl group, or tetrazolyl group, for example 1-tetrazolyl group, which are optionally substituted, for example by lower alkyl, such as methyl, or by amino or aminomethyl which are optionally protected, for example acylated as indicated above, or represents an optionally substituted lower alkoxy group, for example methoxy group, or represents an optionally substituted phenyloxy group, such as a phenyloxy group which contains optionally protected hydroxyl, for example hydroxyl acylated as indicated above, and/or halogen, such as chlorine, or represents a lower alkylthio group, for example a n-butylthio group, or lower alkenylthio group, for example allylthio group, a phenylthio, pyridylthio, for example 4-pyridylthio, 2-imidazolylthio, 1,2,4-triazol-3-ylthio, 1,3,4-triazol-2-ylthio, 1,2,4-thiadiazol-3-ylthio, such as 5-methyl-1,2,4thiadiazol-3-ylthio, 1,3,4-thiadiazol-2-ylthio, or 5-tetrazolythio, such as 1-methyl-5-tetrazolythio group, which are optionally substituted, for example by lower alkyl, such as methyl, or represents a halogen atom, especially a chlorine or bromine atom, or represents an optionally functionally modified carboxyl group, such as lower alkoxycarbonyl, for example methoxycarbonyl or ethoxycarbonyl, nitrile or carbamoyl which is optionally N-substituted, for example by lower alkyl, such as methyl, or phenyl, or represents an optionally substituted lower alkanoyl group, for example an acetyl or propionyl group, or a benzoyl group, or an azido group, and $R^{II}$ and $R^{III}$ represent hydrogen, or n represents 1, $R^I$ represents lower alkyl or a phenyl, furyl, for example 2-furyl, thienyl, for example 2- or 3-thienyl, or isothiazolyl, for example 4-isothiazolyl group, which are optionally substituted, such as substituted by hydroxyl which is optionally acylated, for example as indicated above, and/or by halogen, for example chlorine, or represents a 1,4-cyclohexadienyl group, $R^{II}$ represents optionally protected or substituted amino, for example amino, acylamino, such as lower alkoxycarbonylamino, 2-halogeno-lower alkoxycarbonylamino or optionally substituted phenyl-lower alkoxycarbonylamino, such as phenyl-lower alkoxycarbonyl-amino which contains lower alkoxy, for example methoxy, or nitro, for example tert.-butoxycarbonylamino, 2,2,2-trichloroethoxycarbonylamino, 4-methoxybenzyloxycarbonylamino or diphenylmethoxycarbonylamino, arylsulphonylamino, for example 4-methylphenylsulphonylamino, tritylamino, arylthioamino, such as nitrophenylthioamino, for example 2-nitrophenylthioamino, or tritylthioamino or 2-propylideneamino which is optionally substituted, such as 2-propylideneamino which contains lower alkoxycarbonyl, for example ethoxycarbonyl, or lower alkanoyl, for example acetyl, such as 1-ethoxycarbonyl-2-propylideneamino, or optionally substituted carbamoylamino, such as guanidinocarbonylamino, or a sulphoamino group which is optionally present in the form of a salt, for example in the form of an alkali metal salt, or represents an azido group, or represents a carboxyl group which is optionally present in the form of a salt, for example in the form of an alkali metal salt, or in a protected form, such as in an esterified form, for example as a lower alkoxycarbonyl group, for example a methoxycarbonyl or ethoxycarbonyl group, or as a phenyl-loweralkoxy carbonyl group, for example diphenylmethoxycarbonyl group, or represents a cyano group or a sulpho group or an optionally functionally modified hydroxyl group, wherein functionally modified hydroxyl in particular represents acyloxy, such as formyloxy, as well as lower alkoxycarbonyloxy, 2-halogeno-lower alkoxycarbonyloxy or optionally substitued phenyl-lower alkoxycarbonyloxy, such as phenyl-lower alkoxycarbonyloxy which contains lower alkoxy, for example methoxy, or nitro, for example tert.-butoxycarbonyloxy, 2,2,2-trichloroethoxycarbonyloxy, 4-methoxybenzyloxycarbonyloxy or diphenylmethoxycarbonyloxy, or optionally substituted lower alkoxy, for example methoxy, or pheonoxy, or represents an O-lower alkyl-phosphono or O,O'-di-lower alkyl-phosphono group, for example O-methyl-phosphono or O,O'-dimethylphosphono, or represents a halogen atom, for example chlorine or bromine, and $R^{III}$ represents hydrogen, or $n$ represents 1, $R^I$ and $R^{II}$ each represent halogen, for example bromine, or lower alkoxycarbonyl, for example methoxycarbonyl, and $R^{III}$ represents hydrogen, or $n$ represents 1, $R^I$ represents a phenyl, furyl, for example 2-furyl, or thienyl, for example 2- or 3-thienyl, or isothiazolyl, for example 4-isothiazolyl group, which are optionally substituted, for example by hydroxyl which is optionally acylated, for example as indicated above, and/or by halogen, for example chlorine, or represents a 1,4-cyclohexadienyl group, $R^{II}$ represents aminomethyl which is optionally protected, for example as indicated above, and $R^{III}$ represents hydrogen, or $n$ represents 1 and each of the groups $R^I$, $R^{II}$ and $R^{III}$ represents lower alkyl, for example methyl.

A divalent acyl group formed by the two radicals $R_1{}^a$ and $R_1{}^b$ is, for example, the acyl radical of a lower alkanedicarboxylic acid or lower alkenedicarboxylic acid, such as succinyl, or of an o-arylendicarboxylic acid, such as phthaloyl.

A further divalenet radical formed by the groups $R_1{}^a$ and $R_1{}^b$ is, for example, a 1-oxo-3-aza-4-butylene radical which contains, especially in the 3-position, for example an optionally substituted phenyl or thienyl and optionally contains, in the 4-position, one or preferably two lower alkyl groups, for example 4,4-dimethyl-2-phenyl-1-oxo-3-aza-1,4-butylene.

An organic radical $R_2{}^A$ which forms, together with the —C(=O)—O—grouping, an esterified carboxyl group which can preferably be split easily represents, for example, a 2-halogenolower alkyl radical $R_2{}^a$, wherein halogen has an atomic weight above 19. Such a radical forms, together with the —C(=O)—O— grouping, an esterified carboxyl group which can easily be split on treatment with chemical reducing agents under neutral or weakly acid conditions, for example with zinc in the presence of aqueous acetic acid, or an esterified carboxyl group which can easily be converted into such a group and is, for example, 2,2,2-trichloroethyl or 2-iodoethyl or 2-bromoethyl.

A further group $R_2{}^A$ which together with the —C(=O)—O—grouping represents an esterified carboxyl group which can also be split easily on treatment with chemical reducing agents under neutral or weakly acid conditions, for example on treatment with zinc in the presence of aqueous acetic acid, is an arylcarbonylmethyl group $R_2{}^b$, wherein aryl in particular represents an optionally substituted phenyl group, and preferably phenacyl.

The group $R_2{}^A$ can also represent the radical $R_2{}^c$, which represents an arylmethyl group, wherein aryl in particular denotes a monocyclic aromatic hydrocarbon radical which is suitably substituted. Such a radical forms, together with the —C(=O)—O— grouping, an esterified carboxyl group which can easily be split on irradiation, preferably with ultraviolet light, under neutral or acid conditions. Such an aryl radical in particular contains, as the substituent, lower alkoxy, for example methoxy (which in the case of the preferred phenyl radical is above all in the 3-, 4- and/or 5-position), and/or above all nitro (in the case of the preferred phenyl radical preferably in the 2-position). Such radicals $R_2{}^c$ are above all methoxybenzyl, for example 3- or 4-methoxybenzyl or 3,5-dimethoxybenzyl, nitrobenzyl, for example 2-nitrobenzyl, or methoxy-nitrobenzyl, for example 4,5-dimethoxy-2-nitrobenzyl.

A group $R_2{}^A$ can also represent the radical $R_2{}^d$ which, together with the —C(=O)—O— grouping, forms an esterified carboxyl group which can easily be split solvolytically under acid conditions, for example on treatment with trifluoroacetic acid or formic acid. Such a radical $R_2{}^d$ is above all a methyl group which is polysubstituted by optionally substituted hydrocarbon radicals, especially lower alkyl and/or optionally substituted phenyl or biphenylyl, or is monosubstituted by a heterocyclic group of aromatic character containing oxygen or sulphur atoms as ring members, or denotes a ring member in a polycycloaliphatic hydrocarbon radical or denotes the ring member which represents the α-position relative to the oxygen or sulphur atom in an oxacycloaliphatic or thiacycloaliphatic radical.

Preferred polysubstituted methyl groups $R_2{}^d$ are, for example, tert.-lower alkyl, such as tert.-butyl or tert.-pentyl, optionally lower alkoxy-substituted diphenylmethyl, such as benzhydryl or 4,4'-dimethoxy-benzhydryl, or α-lower alkyl-α-biphenylyl-lower alkyl, for example 2-(4-biphenylyl)-2-propyl, whilst a methyl group $R_2{}^d$ which contains the abovementioned heterocyclic group is, for example, furylmethyl, for example 2-furfuryl. A polycycloaliphatic hydrocarbon radical in which the methyl group $R_2{}^d$ represents a branched, preferably triply branched, ring member is, for example, adamantyl, such as 1-adamantyl, and an abovementioned oxacycloaliphatic or thiacycloaliphatic radical $R_2{}^d$ is 2-tetrahydrofuryl, 2-tetrahydropropyranyl (sic) or 2,3-dihydro-2-pyranyl or corresponding sulphur analogues.

The radical $R_2{}^A$ can also represent a radical $R_2{}^e$, which together with the —C(=O)—O— grouping forms an esterified carboxyl group which can be split hydrolytically, for example under weakly basic or weakly acid conditions. Such a radical $R_2{}^e$ is, preferably, a radical which forms an activated ester with the —C(=O)—O—grouping, such as nitrophenyl, for example 4-nitrophenyl or 2,4-dinitrophenyl, nitrophenyl-lower alkyl, for example 4-nitrobenzyl, polyhalogenophenyl, for example 2,4,6-trichlorophenyl or 2,3,4,5,6-pentachlorophenyl, or cyanomethyl, as well as acylaminomethyl, for example phthaliminomethyl or succinyliminomethyl, trityl or bis-aryloxy-methyl, for example bis-(4-methoxyphenyloxy)-methyl.

The group $R_2{}^A$ can also represent a radical $R_2{}^f$ which together with the carboxyl group —C(—O)—O— forms an esterified carboxyl group which can be split under reductive conditions for example, hydrogenolytically, and is, for example, an optionally substituted α-aryl-lower alkyl radical, such radical, such as benzyl optionally substituted by methoxy or nitro, for example benzyl, 4-methoxy-benzyl or 4-nitrobenzyl, whereby the latter may also be split off chemically, for example, by treatment with zinc and acetic acid or sodium dithionite.

The group $R_2{}^A$ can also represent a radical $R_2{}^g$ which, together with the carboxyl grouping —C(=O)—O—, forms an esterified carboxyl group which can be split under physiological conditions, above all lower alkanoyloxymethyl, for example acetoxymethyl or pivaloyloxymethyl.

A silyl or stannyl radical $R_2^A$ preferably contains optionally substituted aliphatic, cycloaliphatic, aromatic or araliphatic hydrocarbon radicals, such as lower alkyl, cycloalkyl, phenyl or phenyl-lower alkyl groups, and above all represents di-lower alkyl-halogenosilyl, for example chlorodimethyl-silyl, tri-lower alkyl-silyl, for example trimethyl-silyl, or tri-lower alkyl-stannyl, for example tri-n-butyl-stannyl. The radical $R_2^A$ can also represent a bivalent dilower alkylsilyl radical, for example dimethylsilyl, which is bonded to two carboxyl groups —C(=O)—O—.

An acyl radical $R_2^A$ which together with the —C(=O)—O— grouping forms a mixed anhydride group which can be split, preferably hydrolytically, is, for example, the acyl radical of one of the abovementioned organic carboxylic acids or carbonic acid half-derivatives, such as lower alkanoyl, for example acetyl, or lower alkoxycarbonyl, for example ethoxycarbonyl.

Salts are, in particular, those of compounds of the formula I, in which $R_2$ represents hydrogen, above all metal salts or ammonium salts, such as alkali metal salts and alkaline earth metal salts, for example sodium salts, potassium salts, magnesium salts or calcium salts, as well as ammonium salts with ammonia or suitable organic amines, possible amines for forming salts being, above all, aliphatic, cycloaliphatic, cycloaliphatic-aliphatic and araliphatic primary, secondary or tertiary monoamines, diamines or polyamines, as well as heterocyclic bases, such as lower alkylamines, for example triethylamine, hydroxy-lower alkylamines, for example 2-hydroxyethylamine, bis-(2-hydroxyethyl)-amine or tri-(2-hydroxyethyl)-amine, basic aliphatic esters of carboxylic acids, for example 4-aminobenzoic acid 2-diethylaminoethyl ester, lower alkyleneamines, for example 1-ethyl-piperidine, cycloalkylamines, for example bicyclohexylamine, or benzylamines, for example N,N'-dibenzyl-ethylenediamine, and also bases of the pyridine type, for example pyridine, collidine or quinoline. Compounds of the formula I, in which, for example, $R_1^a$ and $R_1^b$ represent hydrogen, or which contain a basic group in a radical $R_1^a$ and $R_1^b$, can also form acid addition salts, for example with inorganic acids, such as hydrochloric acid, sulphuric acid or phosphoric acid, or with suitable organic carboxylic acids or sulphonic acids, for example trifluoroacetic acid. Compounds of the formula I, wherein $R_2$ represents hydrogen, and in which $R_1^a$ and $R_1^b$ denote hydrogen, or which contain a basic group in a radical $R_1^a$ and $R_1^b$, can also be in the form of an inner salt, that is to say in the form of a zwitter-ion.

The compounds of the formula I are known or can, if they are new, be converted into other compounds in a manner which is in itself known. They are, above all, valuable intermediate products for the manufacture of new compounds having pharmacological properties; their conversion into such compounds is described in more detail below.

Particularly valuable intermediate products are compounds of the formfula I, wherein R represents lower alkyl, especially methyl, or represents a monocyclic, five-membered heterocyclic radical of aromatic character which is bonded to the thio sulphur atom via a ring carbon atom and which contains 2 or 3 ring nitrogen atoms and optionally additionally a ring oxygen atom, a ring sulphur atom or a ring nitrogen atom, such a radical optionally being substituted by lower alkyl, especially methyl, or represents an unsaturated monocyclic, 6-membered, heterocyclic radical which is bonded to the thio sulphur atom via a ring carbon atom and contains 2 ring nitrogen atoms, with either one ring nitrogen atom containing an oxido group or one ring carbon atom containing an oxo group, and with such a heterocyclyl radical optionally being substituted by lower alkyl, for example methyl, lower alkoxy, for example methoxy, or halogen, for example chlorine, and wherein $R_1^a$ denotes hydrogen or an acyl radical contained in a fermentatively preparable (that is to say naturally occurring) or bio-synthetically, semi-synthetically or fully synthetically preparable, especially pharmacologically active, such as highly active, N-acyl derivative of a 6-amino-2,2-dimethyl-penam-3-carboxylic acid compound or 7-amino 3-cephem-4-carboxylic acid compound or denotes an easily removable acyl radical of a carbonic acid half-derivative, especially of a carbonic acid half-ester, such as an acyl radical of the abovementioned formula Ia, wherein $R^I$, $R^{II}$, $R^{III}$ and $n$ have the preferred meanings, $R_1^b$ represents hydrogen and $R_2$ represents hydrogen or an organic radical $R_2^A$ which together with the —C(=O)—O— grouping forms an esterified carboxyl group which can easily be split on treatment with water, with an acid agent, with a chemical reducing agent under neutral or weakly acid conditions, hydrolytically, hydrogenolytically or under physiological conditions, or forms an esterified carboxyl group which can be converted into the above esterified carboxyl group, and represents, for example, tri-lower alkyl-silyl, such as trimethyl-silyl, tert.-lower alkyl, such as tert.-butyl or tert.-pentyl, 2-halogeno-lower alkyl, such as 2,2,2-trichloroethyl or 2-iodoethyl, or 2-bromoethyl which can be converted into the latter, arylcarbonylmethyl, such as phenacyl, lower alkoxy-benzyl or nitro-benzyl, such as 2-methoxybenzyl or 4-nitrobenzyl, optionally lower alkoxy-substituted diphenylmethyl, such as diphenylmethyl or 4,4'-dimethoxy-diphenylmethyl, trityl, bis-(lower alkoxyphenoxy)-methyl, such as bis-(4-methoxy-phenoxy)-methyl, or lower alkanoyloxymethyl, such as acetoxymethyl or pivaloyloxymethyl, and also salts of such compounds which have salt-forming groups.

Above all, in a compound of the formula I, R represents methyl or thiadiazolyl which is optionally substituted by lower alkyl, for example methyl, and is bonded to the thio sulphur atom via ring carbon atom, for example 1,3,4-thiadiazol-2-yl, 5-methyl-1,3,4-thiadiazol-2-yl or 5-methyl-1,2,4-thiadiazol-2-yl, or tetrazolyl which is similarly substituted and bonded, for example 1-methyl-5-tetrazolyl, or N-oxidopyridazinyl which is optionally substituted by lower alkyl, for example methyl, lower alkoxy, for example methoxy, or halogen, for example chlorine, and is bonded to the thio sulphur atom via a ring carbon atom, for example 3-methyl-2-oxido-6-pyridazinyl, 3-methoxy-1-oxido-6-pyridazinyl or 3-chloro-1-oxido-6-pyridazinyl, $R_1^a$ represents hydrogen or an acyl radical contained in fermentatively preparable (that is to say naturally occurring) or biosynthetically preparable N-acyl derivatives of 6-amino-2,2-dimethyl-penam-3-carboxylic acid compounds or 7-amino-3-cephem-4-carboxylic acid compounds, such as an optionally substituted phenylacetyl or phenoxyacetyl radical, or an optionally substituted lower alkanoyl or lower alkenoyl radical, for example 4-hydroxy-phenylacetyl, hexanoyl, octanoyl, 3-hexenoyl, 5-amino-5-carboxy-valeryl, n-butylmercaptoacetyl or allylmercaptoacetyl and especially phenylacetyl or phenoxyacetyl, or represents an acyl radical occurring in highly active N-acyl derivatives of 6-amino-2,2-dimethyl-penam-3-carboxylic acid compounds or 7-amino-3-cephem-4-carboxylic acid compounds, for example one of the abovementioned acyl radicals of the formula Ia, such as 2-chloroethylcarbamoyl or cyanoacetyl, but especially phenylglycyl, wherein phenyl represents phenyl optionally substituted by hydroxyl and/or halogen, for example chlorine, for example phenyl, 3- or 4-hydroxyphenyl, 3-chloro-4-hydroxyphenyl or 3,5-dichloro-4-hydroxyphenyl, and wherein the amino group is optionally substituted and for example represents a sulphoamino group which is optionally present in the form of a salt, or an amino group which contains, as substituents, a hydrolytically removable trityl group or an optionally substituted carbamoyl group, such as an optionally substituted ureidocarbonyl group, for example ureidocarbonyl or N³-trichloromethylureidocarbonyl, or an optionally substituted guanidinocarbonyl group, for example guanidinocarbonyl, or an acyl radical which can be split off, preferably easily, for example on treatment with an acid agent, such as trifluoroacetic acid, or with a chemical reducing agent, such as zinc in the presence of aqueous acetic acid, or an acyl radical which can be converted into such a radical, preferably a suitable acyl radical of a carbonic acid half-ester, such as tert.-butoxycarbonyl 2,2,2-trichloroethoxycarbonyl, 2-bromoethoxycarbonyl, 2-iodoethoxycarbonyl or phenacyloxycarbonyl, or of a carbonic acid half-amide, such as carbamoyl or N-methylcarbamoyl, or wherein the amino group is bonded to the nitrogen atom of the 7-amino group by a methylene group which optionally contains lower alkyl, such as two methyls, or 2-thienylacetyl, α-amino-2-thienylacetyl (optionally with an amino group which is substituted, for example as indicated above), or 1-amino-cyclohexylcarbonyl (optionally with an amino group which is substituted, for example as indicated above), as well as α-carboxyphenylacetyl or α-carboxy-2-thienylacetyl (optionally with a functionally modified carboxyl group, for example a carboxyl group present in the form of a salt, such as the sodium salt, or in the form of an ester, such as a lower alkyl ester, for example the methyl ester or ethyl ester, or a phenyl-lower alkyl ester, for example the diphenylmethyl ester), or α-sulpho-phenylacetyl (optionally with a sulpho group which is functionally modified, for example like the carboxyl group), or 2-(1-tetrazolyl)-acetyl and $R_1{}^b$ represents hydrogen, and $R_2$ represents hydrogen or a radical $R_2{}^A$ which together with the —C(=O)—O— grouping forms an esterified carboxyl group which can be split easily on treatment with a chemical reducing agent under neutral or weakly acid conditions, with an acid reagent, hydrolytically (preferably under weakly basic conditions), hydrogenolytically or under physiological conditions, and above all is methyl which is trisubstituted by optionally substituted aromatic or aliphatic hydrocarbon radicals, such as lower alkyl, for example methyl, or is monosubstituted or disubstituted by methyl containing halogen, for example chlorine, bromine or iodine, by benzoyl or lower alkanoyloxy or by phenyl or phenoxy which are optionally substituted, such as phenyl or phenoxy which contain lower alkoxy or nitro, in particular tert.-butyl, diphenylmethyl, 4,4'-dimethoxy-diphenylmethyl, trityl, 2,2,2-trichloroethyl, 2-iodoethyl or 2-chloroethyl or 2-bromoethyl which can easily be converted into 2-iodoethyl, or phenacyl, or 4-methoxybenzyl or 4-nitrobenzyl, and also bis-(4-methoxy-phenoxy)-methyl, acetoxymethyl or pivaloyloxymethyl.

Above all, the invention relates to the manufacture of compounds of the formula I, wherein R represents methyl or thiadiazolyl or tetrazolyl which are optionally substituted by lower alkyl, for example methyl and are bonded to the thio sulphur via a ring carbon atom, for example 1,2,4-thiadiazol-3-yl, 2-methyl-1,3,4-thiadiazol-5-yl or 1-methyl-5-tetrazolyl, $R_1{}^b$ denotes hydrogen, and $R_1{}^a$ denotes hydrogen, or denotes cyanoacetyl, or denotes an acyl group of the formula

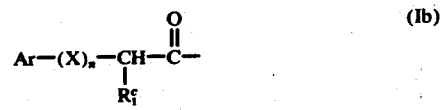

wherein Ar represents phenyl or hydroxyphenyl, for example 3- or 4-hydroxyphenyl, or hydroxy-chlorophenyl, for example 3-chloro-4-hydroxyphenyl or 3,5-dichloro-4-hydroxy-phenyl, it being possible for hydroxy substituents in such radicals to be protected by acyl radicals, such as optionally halogenated lower alkoxycarbonyl radicals, for example tert.-butoxycarbonyl or 2,2,2-trichloroethoxycarbonyl, as well as thienyl, for example 2- or 3-thienyl, and also pyridyl, for example 4-pyridyl, aminopyridinium, for example 4-amino-pyridinium, furyl, for example 2-furyl, isothiazolyl, for example 4-isothiazolyl, tetrazolyl, for example 1-tetrazolyl, or cyclohexadienyl, X represents oxygen or sulphur, n represents 0 or 1 and $R_1{}^c$ represents hydrogen or, if n represents O, also represents optionally protected amino, such as acylamino, for example α-poly-branched lower alkoxycarbonylamino, such as tert.-butoxycarbonylamino, or 2-halogeno-lower alkoxycarbonylamino, for example 2,2,2-trichloroethoxycarbonylamino, 2-iodoethoxycarbonylamino or 2-bromoethoxycarbonylamino, or phenyl-lower alkoxycarbonylamino which is optionally substituted by lower alkoxy or nitro, for example 4-methoxybenzyloxycarbonylamino, or 3-guanylureido, or sulphoamino or tritylamino, or optionally portected carboxyl, for example esterified carboxyl, such as phenyl-lower alkoxycarbonyl, for example diphenylmethoxycarbonyl, optionally protected sulpho, such as sulpho present in the form of an alkali metal salt, for example in the form of the sodium salt, optionally protected hydroxyl, such as acyloxy, for example α-poly-branched lower alkoxycarbonyloxy, such as tert.-butoxycarbonyloxy, or 2-halogeno-lower alkoxycarbonyloxy, such as 2,2,2-trichloroethoxycarbonyloxy, 2-iodoethoxycarbonyloxy or 2-bromoethoxycarbonyloxy, or formyloxy, or O-lower alkylphosphono or O,O-di-lower alkylphosphono, for example O-methylphosphono or O,O-dimethylphosphono, or denotes a 5-amino-5-carboxy-valeryl radical wherein the amino and/or carboxyl groups are optionally protected and are, for example, present as acylamino, for example lower alkanoylamino, such as acetylamino, halogeno-lower alkanoylamino, such as dichloroacetylamino, or phthaloylamino, or as esterified carboxyl, such as phenyl-lower alkoxycarbonyl, for example diphenylmethoxycarbonyl, and $R_2$ represents hydrogen, lower alkyl, especially α-poly-branched lower alkyl, for example tert.-butyl, 2-halogeno-lower alkyl, for example 2,2,2-trichloroethyl, 2-iodoethyl or 2-bromoethyl, nitro-benzyl, for example, 4-nitrobenzyl, or diphenylmethyl which is optionally substituted, for example by lower alkoxy, for example such as methoxy, for example diphenylmethyl or 4,4'-dimethoxydiphenylmethyl, and also salts of such compounds which contain salt-forming groups.

In compounds of the formula I which should be described as being particularly valuable, R represents methyl or thiadiazolyl or tetrazolyl which are optionally substituted by methyl and are bonded to the thio sulphur via a ring carbon atom, for example 1,2,4-thiadiazol-3-yl, 2-methyl-1,3,4-thiadiazol-5-yl or 1-methyl-5-tetrazolyl, $R_1^b$ represents hydrogen, $R_1^a$ represents hydrogen, or represents cyanoacetyl, or represents the acyl radical of the formula Ib, wherein Ar denotes phenyl or 1-tetrazolyl, X denotes oxygen, $n$ denotes 0 or 1 and $R_1^c$ denotes hydrogen or, if $n$ represents 0, denotes optionally substituted amino, such as acylamino, for example α-poly-branched lower alkoxycarbonylamino, such as tert.-butoxycarbonylamino, or 2-halogeno-lower alkoxycarbonylamino, for example 2,2,2-trichloroethoxycarbonylamino, 2-iodoethoxycarbonylamino or 2-bromoethoxycarbonylamino, or phenyl-lower alkoxycarbonylamino which is optionally substituted by lower alkoxy or nitro, for example 4-methoxybenzyloxycarbonylamino, or optionally protected hydroxyl, such as acyloxy, for example α-poly-branched lower alkoxycarbonyloxy, such as tert.-butoxycarbonyloxy, or 2-halogeno-lower alkoxycarbonyloxy, such as 2,2,2-trichloroethoxycarbonyloxy, 2-iodoethoxycarbonyloxy or 2-bromoethoxycarbonyloxy or formyloxy, or represents a 5-amino-5-carboxyvaleryl radical, wherein the amino and/or carboxyl group are optionally protected and are present, for example, as acylamino, for example lower alkanoylamino, such as acetylamino, halogeno-lower alkanoylamino, such as dichloroacetylamino, or phthaloylamino, or as esterified carboxyl, such as phenyl-lower alkoxycarbonyl, for example diphenylmethoxycarbonyl, and $R_2$ denotes hydrogen, lower alkyl which is optionally substituted in the 2-position by halogen, for example chlorine, bromine or iodine, especially α-poly-branched lower alkyl, for example tert.-butyl, or 2-halogeno-lower alkyl, for example 2,2,2-trichloroethyl, 2-iodoethyl or 2-bromoethyl, nitrobenzyl, for example, 4-nitro-benzyl, or optionally lower alkoxy-substituted, such as methoxy-substituted, diphenylmethyl, for example diphenylmethyl or 4,4'-dimethoxy-diphenylmethyl.

The compounds of the formula I are obtained in a surprising manner and with excellent yields when a 7-(N-$R_1^A$-N-$R_1^b$-amino)-3-Y-methyl-2-cephem-4ξ-carboxylic acid compound of the formula

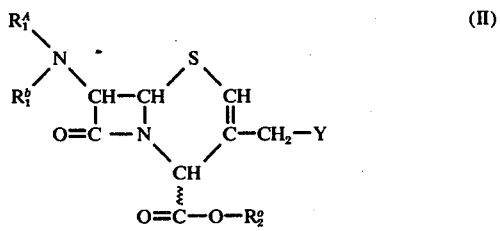

(II)

wherein $R_1^A$ and $R_1^b$ have the abovementioned meanings, and $R_1^A$ and $R_1^b$ can also together denote a bivalent amino protective group, $R_2^o$ represents hydrogen or radical which together with the —C(=O)—O— grouping forms an esterified carboxyl group, and Y represents a free or esterified hydroxyl group, is reacted with a compound of the formula R—SH (III), with the proviso that if a starting material of the formula II, wherein Y represents a free hydroxyl group or an esterified hydroxyl group other than the trifluoroacetoxy group, the reaction is carried out in the presence of an optionally protonic Lewis acid and, if desired, in a compound obtainable in accordance with the process, amino protective groups $R_1^A$ and/or $R_1^b$ are split off, and/or, if desired, in a compound obtainable, which has a free amino group, the latter is protected, and/or, if desired, in a compound obtainable according to the process, an esterified carboxyl group is converted into a free carboxyl group or into a protected carboxyl group, and/or, if desired, in a compound obtainable according to the process a free carboxyl group is converted into a protected carboxyl group of the formula —C(=O)—O—$R_2^A$ and/or, if desired, a compound obtainable according to the process and having a salt-forming group is converted into a salt, or a salt obtained is converted into the free compound or into another salt, and/or, if desired, an isomer mixture obtainable according to the process is separated into the individual isomers.

In a starting material of the formula II, an esterified hydroxyl group Y is preferably esterified by an organic carboxylic acid, and the latter represents an aliphatic carboxylic acid (including formic acid), or a cycloaliphatic, cycloaliphatic-aliphatic, aromatic, araliphatic, heterocyclic or heterocyclic-aliphatic carboxylic acid, or a carbonic acid half-derivative, such as one of the acids or carbonic acid half-esters mentioned.

Thus, an esterified hydroxyl group Y can represent optionally substituted lower alkanoyloxy, especially acetoxy, or halogeno-lower alkanoyloxy, especially halogenoacetoxy, such as trifluoroacetoxy or dichloroacetoxy, and also formyloxy.

The starting material of the formula II can be used in the form of the free carboxylic acids, that is to say $R_2^o$ usually represents hydrogen. However, it is also possible to employ compounds of the formula II, in which $R_2^o$ differs from hydrogen and represents, for example, a radical which together with the —C(=O)—O— grouping forms an esterified carboxyl group which is stable under the reaction conditions, for example in the presence of a Lewis acid which may be used, or an esterified carboxyl group which can be split under the reaction conditions, including a silylated or stannylated carboxyl group, for example one of the abovementioned corresponding groups $R_2^A$.

Free functional groups, for example free hydroxyl, mercapto and/or amino groups, which do not participate in the reaction, especially those present in an amino protective group $R_1^A$ and/or $R_1^b$, can be protected in the starting materials if necessary, for example by acyl or trityl groups or by organic silyl groups, in a manner which is in itself known, for example temporarily, and can, if desired, be liberated in a manner which is in itself known, during the reaction or after the reaction has taken place.

The compounds of the formula III are the corresponding mercaptans, such as lower aliphatic mercaptans, especially lower alkylmercaptans, above all methylmercaptan, or heterocyclic mercaptans, in which the mercapto group is bonded to a ring carbon atom and the heterocyclic ring contains 1–4 ring nitrogen atoms and optionally a further ring hetero-atom from the group of oxygen and sulphur.

Depending on the nature of the radical Y in the starting material of the formula II, the process according to the invention can be carried out in the presence or absence of optionally protonic Lewis acids. If the group Y represents the trifluoroacetoxy group, the reaction can, if desired, be carried out in the absence of such Lewis acids but can also be carried out in their presence.

If starting materials of the formula II are used, wherein Y generally denotes a free hydroxyl group or a hydroxyl group esterified by an organic carboxylic acid other than trifluoroacetic acid, that is to say also including a hydroxyl group esterified by a relatively weak acid, such as a weak lower alkanecarboxylic acid, for example acetic acid, propionic acid or pivalic acid, or an arylcarboxylic acid, for example benzoic acid, that is to say wherein Y denotes a free hydroxyl group or a lower alkanoyloxy group, especially an acetoxy or propionyloxy or pivaloyloxy group, or an aroyloxy group, for example a benzoyloxy group, the reaction of such a starting material of the formula II with the mercaptan of the formula III is carried out in the presence of an optionally protonic Lewis acid. Of course, starting materials of the formula II, wherein Y represents a trifluoroacetoxy group, can also be used in the presence of such an acid.

Suitable protonic Lewis acids are, above all, for example, strong, non-nucleophilic or only weakly nucleophilic, inorganic acids, such as phosphoric acid, preferably in the form of polyphosphoric acid, fluoboric acid or perchloric acid, the latter, for example, together with an organic carboxylic acid, such as an optionally substituted lower alkanecarboxylic acid, preferably acetic acid, and also sulphuric acid. Preferred protonic Lewis acids are strong, non-nucleophilic or only weakly nucleophilic organic carboxylic acids, such as lower alkanecarboxylic acids which are optionally suitably substituted, for example by halogen atoms or cyano groups, such as formic acid, halogenated lower alkanecarboxylic acids, which preferably contain several halogen atoms, for example fluorine or chlorine atoms, in the α-position, above all trifluoroacetic acid, and also cyanoacetic acid, as well as strong non-nucleophilic or only weakly nucleophilic organic sulphonic acids, such as lower alkanesulphonic acids, for example methanesulphonic acid, or benzenesulphonic acids which are optionally substituted, for example by lower alkyl groups, for example p-toluenesulphonic acid.

Non-protonic Lewis acids, which at most have slight nucleophilic properties, are, above all, non-nucleophilic or only weakly nucleophilic halides of Lewis acid character, such as boron halides, especially boron trifluoride, and also boron trichloride or boron tribromide, it also being possible to use, for example, boron trifluoride as the etherate, for example as the diethyl etherate, as well as aluminium halides, for example aluminium chloride, or tin-IV halides, for example tin-IV chloride.

In the above process variant, according to which the reaction is carried out in the presence of a Lewis acid, easily protonisable groups in the starting materials of the formula II are preferably present in a non-protonisable form or in a form which can only be protonised with difficulty. Examples of easily protonisable groups are basic amino groups; these can, for example, be present in the form of acylamino groups, inter alia also those which can subsequently be split easily, for example by reduction or solvolysis, for example in the form of 2,2,2-trichloroethoxycarbonyl-amino or tert.-butoxycarbonylamino groups, of tritylamino groups or of organic silylamino groups, for example trimethylsilylamino groups.

The reaction can be carried out in the absence or presence of a solvent or diluent, and suitable reactants, such as trifluoroacetic acid, can also be used as the solvents or diluents. Furthermore it is possible, for example, to use, as optional additional inert solvents or diluents, optionally substituted hydrocarbons, such as lower aliphatic, cycloaliphatic or aromatic hydrocarbons which are optionally halogenated or contain cyano groups, for example hexane, methylene chloride, chloroform, acetonitrile, cyclohexane, benzene or toluene. The reaction is carried out with cooling, at room temperature or with warming, preferably in a temperature range from about $-30°$ to about $+100°$ C and, if necessary, in a closed vessel and/or in an inert gas atmosphere, for example a nitrogen atmosphere.

In a compound of the formula I obtainable in accordance with the process, a triarylmethyl protective group $R_1^A$ of an amino group can be split off under acid conditions, for example in the presence of an inorganic acid, such as hydrochloric acid, and be replaced by hydrogen.

In a resulting compound, an acyl radical Ac present as an amino protective group $R_1^A$ and/or $R_1^b$ can be split off in a manner which is in itself known. Thus, an easily removable acyl radical of a carbonic acid half-ester can be split off under mild conditions which do not affect the remainder of the molecule, tert.-butoxycarbonyl, for example, by treatment with trifluoroacetic acid (optionally under the reaction conditions) and 2,2,2-trichloroethoxycarbonyl, 2-iodoethoxycarbonyl or phenacyloxycarbonyl, for example, by treatment with a suitable reducing metal or a reducing metal compound, for example zinc or a chromium-II salt, such as chromium-II chloride or chromium-II acetate, advantageously in the presence of a hydrogen donor which together with the metal or metal compound generates nascent hydrogen, preferably aqueous acetic acid.

Furthermore, in a resulting compound of the formula I, wherein a carboxyl group $-C(=O)-O-R_2$ preferably represents a carboxyl group which is protected, for example by esterification, including by silylation or stannylation (for example by reaction with a suitable organic halogenosilane compound or halogeno-tin-IV compound, such as trimethylchlorosilane or tri-n-butyl-tin chloride) or is present in the form of a salt, for example in the form of a metal salt or ammonium salt, a suitable acyl group Ac, wherein free functional groups which may be present are optionally protected, can be split off by treatment with an imide-halide-forming agent, preferably in the presence of a base, reaction of the resulting imide-halide with an alcohol and splitting of the resulting imino-ether in an aqueous or alcoholic medium, preferably under acid conditions.

Imide-halide-forming agents are those in which halogen is bonded to an electrophilic central atom, above all acid halides, such as acid bromides and especially acid chlorides. They are, primarily, acid halides of inorganic acids, above all of acids containing phosphorus, primarily phosphorus pentachloride, and also acid halides, especially acid chlorides, of acids containing sulphur or of carboxylic acids.

The reaction with an imide-halide-forming agent is preferably carried out in the presence of a suitable base, especially in organic base, above all a tertiary amine, for example a tertiary aliphatic monoamine or diamine, such as a tri-lower alkylamine, for example triethylamine or ethyldiisopropylamine, or a N,N,N',-N'-tetra-lower alkyl-lower alkylenediamine, for example N,N,N',N'-tetramethyl-1,6-hexylenediamine, a monocyclic or bicyclic monoamine or diamine, such as a N-substituted, for example N-lower alkylated, alkyleneamine, azaalkyleneamine or oxaalkyleneamine, for example N-methyl-piperidine or N-methyl-morpholine, or 2,3,4,6,7,8-hexahydro-pyrrolo[1,2-a]pyrimidine (diazabicyclononene; DBN) or, above all, a tertiary heterocyclic, monocyclic or bicyclic, base, such as a quinoline or isoquinoline but especially pyridine. Approximately equimolar amounts of the imide-halide-forming agent and of the base can be used. However, the latter can also be present in excess or in less than equivalent amount, for example in from about 0.2 times the equivalent amount to the equivalent amount, or in up to about a 10-fold excess, especially about a 3-fold to 5-fold excess.

The reaction with the imide-halide-forming agent is preferably carried out with cooling, for example at temperatures of about $+10°$ to about $-50°$ C, but the reaction can also be carried out at higher temperatures, that is to say, for example, up to about $75°$ C, if the stability of the starting materials and the stability of the products permit a higher temperature.

The imide-halide product, which is usually converted further without being isolated, is reacted, according to the process, with alcohols, preferably in the presence of the abovementioned bases, to give the imino-ether. Examples of alcohols are aliphatic alcohols, above all optionally substituted, such as halogenated, for example chlorinated, lower alkanols or alkanols containing additional hydroxyl groups, for example ethanol, n-propanol, isopropanol or n-butanol, but especially methanol, and also 2,2,2-trichloroethanol. Usually an excess, for example an up to about 100-fold excess, of the alcohol is employed, and preferably the reaction is carried out with cooling, for example at temperatures of about $10°$ to about $-50°$ C.

The imino-ether product can advantageously be subjected to the splitting reaction without being isolated. The splitting of the imino-ether to the corresponding compound of the formula I, wherein $R_1^a$ and $R_1^b$ denote hydrogen, can be achieved by solvolysis with a suitable hydroxy compound. For this, preferably water or an alcohol, especially a lower alkanol, for example methanol or ethanol, or an aqueous mixture thereof are used. The reaction is usually carried out in an acid medium, for example at a pH-value of about 1 to about 5, which can be obtained, if necessary, by adding a basic agent, such as an aqueous alkali metal hydroxide, for example sodium hydroxide or potassium hydroxide, or an acid, for example a mineral acid or organic acid, such as hydrochloric acid, sulphuric acid, phosphoric acid, fluoboric acid, trifluoroacetic acid or p-toluenesulphonic acid.

The three-stage process described above is advantageously carried out without isolating the imide-halide and imino-ether intermediate products, usually in the presence of an organic solvent which is inert towards the reactants, such as an optionally halogenated hydrocarbon, for example methylene chloride, and/or in an inert gas atmosphere, such as a nitrogen atmosphere.

If the imide-halide intermediate product obtainable in accordance with the above process is reacted with a salt, such as an alkali metal salt, of a carboxylic acid, especially of a sterically hindered carboxylic acid, instead of being reacted with an alcohol, a N,N-diacylamino compound of the formula I, wherein $R_1^a$ and $R_1^b$ represent acyl groups, is obtained.

In a compound employed in the above acylamino splitting reaction and having a carboxyl group protected by a silyl grouping or a stannyl grouping, these groupings can also be liberated in the course of the splitting of the acylamino grouping, especially in the presence of an alcohol or of water.

In a compound of the formula I, wherein $R_1^a$ and $R_1^b$ together with the nitrogen atom represent a phthalimido group, the latter can be converted into the free amino group, for example by hydrazinolysis, that is to say on treating such a compound with hydrazine.

In a compound of the formula I, wherein $R_1^a$ and $R_1^b$ represent acyl groups, one of these groups, preferably the sterically less hindered group, can be removed selectively, for example by hydrolysis or aminolysis.

Certain acyl radicals of an acylamino grouping in compounds obtainable according to the invention, especially the 5-amino-5-carboxyvaleryl radical, can also be split off by treating them with a nitrosylating agent, such as nitrosyl chloride, with a carbocyclic arenediazonium salt, such as benzenediazonium chloride, or with an agent which provides positive halogen, such as a N-halogen-amide or -imide, for example N-bromosuccinimide, preferably in a suitable solvent or solvent mixture, such as formic acid together with a nitro-lower alkane or cyano-lower alkane, mixing the reaction products with a hydroxylic agent, such as water or a lower alkanol, for example methanol, and, if desired, working up the free amino compound in accordance with methods which are in themselves known.

A formyl group $R_1^A$ can also be split off by treatment with an acid agent, for example p-toluenesulphonic acid or hydrochloric acid, with a weakly basic agent, for example dilute ammonia, or with a decarbonylating agent, for example tris-(triphenylphosphine)-rhodium chloride.

In a compound of the formula I, wherein $R_1^a$ and $R_1^b$ represent hydrogen or together represent an ylidene group, the free amino group can be protected in a manner which is in itself known, for example can be acylated. For this purpose, for example, the customary acylating methods are used, such as treatment with carboxylic acids or reactive acid derivatives thereof, such as halides, for example fluorides or chlorides, or anhydrides (whereby there are also to be understood the inner anhydrides of carboxylic acids, that is to say ketenes, or of carbamic acids or thiocarbamic acids, that is to say isocyanates or isothiocyanates, or mixed anhydrides, such as those which can be formed, for example, with chloroformic acid lower alkyl esters, such as chloroformic acid ethyl ester or isobutyl ester, or halogenoacetic acid halides, such as trichloroacetic acid chloride, or N-carboxyanhydrides which can be formed by reaction of α-aminocarboxylic acids, usable as acylating agents, with phosgene) or activated esters, such as cyanomethyl esters or 4-nitrophenyl esters, or a N-substituted N,N-diacylamine, such as a N,N-diacylated aniline. If necessary, the reaction is carried out in the presence of suitable condensation agents, for example of carbodiimides, such as dicyclohexylcarbodiimide, when acids are used, and, for example, of basic agents, such as triethylamine or pyridine, when reactive acid derivatives are used. The starting material to be acylated can be used in the form of the free acid or in the form of a derivative having a protected carboxyl group, and also in the form of a salt, such as an ammonium salt, for example a tri-lower alkylammonium salt, such as a triethylammonium salt.

An acyl group can also be introduced by reacting a compound of the formula I, wherein $R_1^a$ and $R_1^b$ represent hydrogen, with an aldehyde, such as an aliphatic, aromatic or araliphatic aldehyde, acylating the resulting Schiff's base, for example in accordance with the abovementioned methods, and hydrolysing the acylation product, preferably in a neutral or weakly acid medium.

An acyl group can also be introduced stepwise. Thus it is possible, for example, to introduce, into a compound of the formula I having a free amino group, a halogeno-lower alkanoyl group, for example a bromoacetyl group, or, for example by treatment with a carbonic acid dihalide, such as phosgene, a halogenocarbonyl group, for example the chlorocarbonyl group, and to react a N-(halogeno-lower alkanoyl)-amino or N-(halogenocarbonyl)-amino compound, thus obtainable, with suitable exchange reagents, such as basic compounds, for example tetrazole, thio compounds, for example 2-mercapto-1-methyl-imidazole, or metal salts, for example sodium azide, or alcohols, such as lower alkanols, for example tert.-butanol, and thus to arrive at substituted N-lower alkanoylamino or N-hydroxycarbonylamino compounds. Furthermore it is possible, for example, to react a compound of the formula I, wherein $R_1^b$ represents hydrogen and $R_1^a$ represents a glycyl group which is optionally substituted in the α-position, such as phenylglycyl, with a lower alkanal or lower alkanone, for example formaldehyde or acetone, and thus to arrive at compounds of the formula I, wherein $R_1^a$ and $R_1^b$ together represent a 1-oxo-3-aza-1,4-butylene radical which is optionally substituted in the 2-and/or 4-position.

The acylation can also be effected by replacing an already existing acyl group by another acyl group, preferably a sterically hindered acyl group, for example in accordance with the process described above, by preparing the imide-halide compound, treating the latter with a salt of an acid and hydrolytically splitting off one of the acyl groups present in the product thus obtainable, usually the sterically less hindered acyl group.

In both reactants, free functional groups can be temporarily protected, during the acylation reaction, in a manner which is in itself known, and be liberated, after the acrylation, by means of methods which are in themselves known.

In a compound of the formula I, wherein $R_1^a$ and $R_1^b$ represent hydrogen, the free amino group can also be protected by introducing a triarylmethyl group, for example by treatment with a reactive ester of a triarylmethanol, such as trityl chloride, preferably in the presence of a basic agent, such as pyridine, or by introducing an organic silyl or stannyl radical, for example in accordance with the process shown below.

In a compound of the formula I obtainable in accordance with the process and having a group of the formula $-C(=O)-O-R_2$, wherein $R_2$ represents hydrogen, the free carboxyl group can be esterified in a manner which is in itself known to form a protected carboxyl group, for example by treatment with a diazo compound, such as a diazo-lower alkane, for example diazomethane or diazoethane, or with a phenyl-diazo-lower alkane, for example phenyldiazomethane or diphenyldiazomethane, or by reaction with an alcohol suitable for esterification, in the presence of an esterifying agent, such as a carbodiimide, for example dicyclohexylcarbodiimide or carbonyldiimidazole, or in accordance with any other known and suitable esterification process, such as reaction of a salt of the acid with a reactive ester of an alcohol and a strong inorganic acid or a strong organic sulphonic acid. Furthermore, acid halides, such as acid chlorides (prepared, for example, by treatment with oxalyl chloride), or activated esters (formed, for example, with N-hydroxy-nitrogen compounds or, for example, with halogenoformic acid lower alkyl esters, such as chloroformic acid ethyl ester, or with halogenoacetic acid halides, such as trichloroacetic acid chloride), or mixed anhydrides can be converted into an esterified carboxyl group by reaction with alcohols, if appropriate in the presence of a base, such as pyridine.

Carboxyl groups protected by organic silyl or stannyl groups can be formed in a manner which is in itself known, for example by treating compounds of the formula I, wherein $R_2$ represents hydrogen, or salts, such as alkali metal salts, for example sodium salts, thereof, with a suitable silylating agent, such as a di-lower alkyl-dihalogenosilane, for example dimethyldichlorosilane, tri-lower alkyl-silyl halide, for example trimethyl-silyl chloride, or a N-mono-lower alkylated, N,N-di-lower alkylated, N-tri-lower alkylsilylated or N-lower alkyl-N-tri-lower alkylsilylated N-(tri-lower alkyl-silyl)amine (see, for example, British Patent No. 1,073,530), or with a suitable stannylating agent, such as a bis-(tri-lower alkyl-tin) oxide, for example bis-(tri-n-butyl-tin) oxide, a tri-lower alkyl-tin hydroxide, for example triethyl-tin hydroxide, a tri-lower alkyl-lower alkoxy-tin compound, tetra-lower alkoxy-tin compound or tetra-lower alkyl-tin compound or a tri-lower alkyl-tin halide, for example tri-n-butyl-tin chloride (see, for example, Netherlands Published Specification No. 67/17,107).

Mixed anhydrides can be prepared by reacting a compound of the formula I, wherein $R_2$ represents hydrogen, but preferably a salt thereof, especially an alkali metal salt or ammonium salt thereof, with a reactive derivative, such as a halide, for example the chloride, of an acid, for example a halogenoformic acid lower alkyl ester or a lower alkanecarboxylic acid chloride.

In a resulting compound, a grouping of the formula $-C(=O)-O-R_2^A$ can be converted into another grouping of this formula, for example 2-chloroethoxycarbonyl or 2-bromoethoxy-carbonyl of the formula $-C(=O)-O-R_2^a$ can be converted into 2-iodoethoxy-carbonyl by treatment with an iodine salt, such as sodium iodide, in the presence of a suitable solvent, such as acetone.

In a compound of the formula I obtainable in accordance with the process and having an esterified carboxyl group, the latter representing, for example, an esterified carboxyl group of the formula $-C(=O)-O-R_2^A$ which can easily be converted into the free carboxyl group, this esterified carboxyl group can be converted into the free carboxyl group in a manner which is in itself known, for example in accordance with the nature of the esterifying radical $R_2^A$, a grouping of the formula $-C(=O)-OR_2^a$ or $-C(=O)-OR_2^b$, for example, by treatment with a chemical reducing agent, such as a metal, for example zinc, or a reducing metal salt, such as a chromium-II salt, for example chromium-II chloride, usually in the presence of a hydrogen donor which can generate nascent hydrogen together with the metal, such as an acid, above all acetic acid or formic acid, or an alcohol, water being added preferably, a grouping of the formula —C(=O)—OR$_2^c$, for example, by irradiation, preferably with ultraviolet light, shorter wavelength ultraviolet light, for example below 290 m$\mu$, being used if R$_2^c$ represents, for example a benzyl radical which is optionally substituted in the 3-, 4- and/or 5-position, for example by lower alkoxy groups and/or nitro groups, or longer wavelength ultraviolet light, for example above 290 m$\mu$, being used if R$_2^c$ denotes, for example, a benzyl radical substituted in the 2-position by a nitro group, a grouping —C(=O)—OR$_2^d$, for example, by solvolysis with a suitable acid agent, such as formic acid or trifluoroacetic acid, if appropriate with addition of a nucleophilic compound, such as phenol or anisole, a grouping —C(=O)—OR$_2^e$ by hydrolysis, for example by treatment with a weakly acid or in particular with a weakly basic aqueous agent, such as aqueous sodium bicarbonate or an aqueous potassium phosphate buffer of pH about 7 to about 9, and a grouping —C(=O)—OR$_2^f$ by hydrogenolysis, for example by treatment with hydrogen in the presence of a noble metal catalyst, for example a palladium catalyst, or, in the care of a 4-nitro-benzylgroup R$_2^f$, also with zinc and acetic acid or a sodium dithionite. A carboxyl group which is protected, for example by silylation or stannylation, can be liberated in the usual manner, for example by treatment with water or an alcohol.

Salts of compound of the formula I can be prepared in a manner which is in itself known. Thus, salts of compounds of the formula I, wherein R$_2$ represents hydrogen, can be formed, for example, by treatment with metal compounds, such as alkali metal salts of suitable carboxylic acids, for example the sodium salt of $\alpha$-ethyl-caproic acid, or with ammonia or a suitable organic amine, preferably using stoichiometric amounts or only a small excess of the salt-forming agent. Acid addition salts of compounds of the formula I which have basic groupings are obtained in the customary manner, for example by treatment with an acid or a suitable anionic exchange reagent. Inner salts of compounds of the formula I, which contain a salt-forming amino group and a free carboxyl group, can be formed, for example, by neutralisation of salts, such as acid addition salts, to the isoelectric point, for example with weak bases, or by treatment with liquid ion exchangers.

Salts can be converted into the free compounds in the usual manner, metal salts and ammonium salts, for example, by treatment with suitable acids, and acid addition salts, for example, by treatment with a suitable basic agent.

Resulting mixtures of isomers can be separated into the individual isomers in accordance with methods which are in themselves known, for example by fractional crystallisation, adsorption chromatography (e.g. column chromatography or thin layer chromatography) or other suitable separation processes. Resulting racemates can be separated into the antipodes in the usual manner, if necessary after introducing suitable salt-forming groupings, for example by forming a mixture of diastereoisomeric salts with optically active salt-forming agents, separating the mixture into the diastereoisomeric salts and converting the separated salts into the free compounds, or by fractional crystallisation from optically active solvents.

The process also encompasses those embodiments according to which compounds which arise as intermediate products are used as starting materials and the remaining process steps are carried out with these, or the process is discontinued at any stage; furthermore, starting materials can be used in the form of derivatives or be formed during the reaction.

Preferably, those starting materials are used, and the reaction conditions are so chosen that the compounds listed initially as being particularly preferred are obtained.

The starting materials of the formula II used in the process are known and can be prepared in accordance with processes which are in themselves known. Thus they are obtained, for example, by treating 7-N-R$_1^a$-N-R$_1^b$-amino-cephalosporanic acid compounds, wherein at least one of the radicals R$_1^a$ and R$_1^b$ preferably represents an amino protective group having the abovementioned meaning and above all represents an acyl radical Ac, with a suitable basic agent, such as pyridine, if appropriate with addition of triethylamine. Preferably, the free 7-N-R$_1^a$-N-R$_1^b$-amino-cephalosporanic acids are used, which, for example, are isomerised in the presence of pyridine and acetic anhydride and give pyridinium salts of 7-N-R$_1^a$-N-R$_1^b$-amino-ceph-2-em-4$\xi$-carboxylic acids which on acidification, for example with phosphoric acid, can be converted into the free compounds. The 7-N-R$_1^a$-N-R$_1^b$-amino-isocephalosporanic acid compounds thus obtainable can, if desired, be converted into other compounds of the formula II. Thus, for example, the free carboxyl group can be converted into a protected carboxyl group and a protected amino group can be converted into a free amino group and this, in turn, into a protected, preferably acylated, amino group; these reactions can be carried out in accordance with the methods described above. The acetoxymethyl group present in the 3-position of the 7-N-R$_1^a$-N-R$_1^b$-amino-isocephalosporanic acid compounds can be converted into the hydroxymethyl group, for example by treatment with an esterase, such as a corresponding enzyme from *Rhizobium trifolii*, *Rhizobium lupinii*, *Rhizobium japonicum* or *Bacterium subtilis*, or by leaving the compound to stand in a weakly basic aqueous solution at pH 9–10, usually a corresponding aqueous sodium hydroxide solution. The compounds of the formula II can also be obtained by total synthesis, for example in accordance with the process described in British Pat. No. 1,155,024. 3-Hydroxymethyl- or 3-acetoxymethyl-7-N-R$_1^a$-N-R$_1^b$-amino-2-cephem-4$\xi$ carboxylic acid compounds can be converted into other 7-N-R$_1^a$-N-R$_1^b$-amino-2-cephem-4-carboxylic acid compounds of the formula II, having esterified hydroxy-methyl groups in the 3-position, by esterification or transesterification in a manner which is in itself known, for example also including treatment with a strong organic carboxylic acid, such as trifluoroacetic acid.

At any suitable stage in the manufacture of the starting materials, additional measures can be carried out on intermediate products, by means of which these can be converted into other intermediate products of the same type; additional measures of this type are, for example, the processes described above and used in conversions of the end products.

In manufacturing the starting materials it is possible, where necessary, temporarily to protect free functional groups in the reactants which do not participate in the reaction, for example free hydroxyl, mercapto and amino groups by, for example, tritylation, acylation or silylation, and free carboxyl groups by, for example, esterification, including silylation, in a manner which is in itself known, and to liberate these groups, in a manner which is in itself known, in each case after the reaction has taken place.

The ceph-2-em compounds of the formula I can, as has already been explained above, be used as intermediate products. Thus they can be converted, in a manner which is in itself known, into the corresponding 7-N-$R_1^a$-N-$R_1^b$-amino-3-R-thio-methyl-3-cephem-4-carboxylic acid compounds of the formula

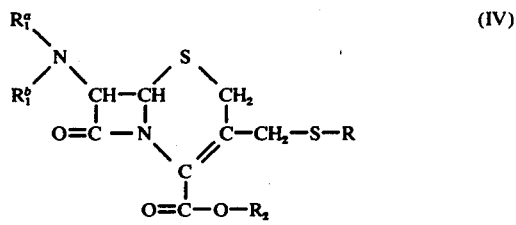

especially into the 3-cephem compounds of the formula IV, which correspond to the 2-cephem compounds of the formula I which have been described as being particularly valuable.

The compounds of the formula IV are obtained by isomerising the 2-cephem compounds of the formula I to the 3-cephem compounds. In the isomerisation of the 2-cephem compounds of the formula I to the corresponding 3-cephem compounds of the formula IV, it is possible to employ compounds of the formula I in which the grouping of the formula —C(=O)—O—$R_2$ represents a free or protected carboxyl group, above all an esterified carboxyl group or a carboxyl group present as a mixed anhydride grouping; furthermore, a protected carboxyl group can also be formed during the reaction.

Thus it is possible to isomerise compounds of the formula I by treating them with a suitable basic agent and isolating the ceph-3-em compound of the formula IV. Examples of such isomerising agents are organic nitrogen-containing bases, especially tertiary aliphatic or azacycloaliphatic bases, such as tri-lower alkylamines, for example triethylamine or N,N-diisopropyl-N-ethylamine, or N-lower alkyl-azacycloalkanes, for example N-methyl-piperidine, as well as tertiary heterocyclic bases of aromatic character, above all bases of the pyridine type, such as pyridine itself, as well as tertiary aromatic bases, such as those of the aniline type, for example N,N-dimethylaniline and mixtures of such bases, such as the mixture of a base of the pyridine type and a N,N,N-trialkylamine, for example pyridine and triethylamine.

The above isomerisation with basic agents can be carried out, for example, in the presence of a derivative of a carboxylic acid which is suitable for forming a mixed anhydride, such as in the presence of a carboxylic acid anhydride or carboxylic acid chloride, for example with pyridine in the presence of acetic anhydride. It is preferably carried out in an anhydrous medium, in the presence or absence of a solvent, such as an optionally halogenated, for example chlorinated, aliphatic, cycloaliphatic or aromatic hydrocarbon, or of a solvent mixture, it also being possible for bases which are used as reactants and are liquid under the reaction conditions to serve simultaneously as the solvent, with cooling, at room temperature or with heating, preferably in a temperature range of about −30° to about +100° C, in an inert gas atmosphere, for example a nitrogen atmosphere, and/or in a closed vessel.

The ceph-3-em compounds obtainable in accordance with the process can be separated from 2-cephem starting material which may still be present, in a manner which is in itself known, for example by adsorption and/or crystallisation.

The isomerisation of the 2-cephem compounds of the formula I can also be carried out by oxidising compounds of the formula I in the 1-position and reducing the 1-oxides of the corresponding 3-cephem compounds of the formula IV, thus obtainable.

Suitable oxidising agents which can be used for the oxidation, in the 1-position, of compounds of the formula I are inorganic per-acids which have a reduction potential of at least + 1.5 volts and consist of non-metallic elements, organic percarboxylic acids or persulphonic acids and mixtures of hydrogen peroxide and acids having a dissociation constant of at least $10^{-5}$, for example periodic acid and persulphuric acid, or performic acid, peracetic acid, pertrifluoroacetic acid, permaleic acid, perbenzoic acid, 3-chloroperbenzoic acid, monoperphthalic acid or p-toluene-persulphonic acid. The oxidation can also be carried out using hydrogen peroxide and catalytic amounts of an organic carboxylic acid having a dissociation constant of at least $10^{-5}$, in which case it is possible to use low concentrations, for example 1–2% and less, but also larger amounts, of the acid; examples of suitable mixtures are those of hydrogen peroxide with acetic acid, perchloric acid or trifluoroacetic acid.

The above oxidation can be carried out in the presence of suitable catalysts. Thus, for example, the oxidation with percarboxylic acids can be catalysed by the presence of an acid having a dissociation constant of at least $10^{-5}$, for example acetic acid, perchloric acid and trifluoroacetic acid. Usually, at least equimolar amounts of the oxidising agent are used, and preferably a slight excess of about 10% to about 20% is employed, though larger excesses, that is to say up to a 10-fold amount of the oxidising agent, or above, can also be used. The oxidation is carried out under mild conditions, for example at temperatures of about −50° C to about +100° C, preferably of about −10° C to about +40° C, in particular in the presence of a suitable solvent or diluent, such as an optionally halogenated, for example chlorinated, or hydroxylated aliphatic, cycloaliphatic or aromatic hydrocarbon, for example methylene chloride, chloroform or isopropanol.

In the resulting 3-cephem-1-oxide intermediate compounds, which correspond to the compounds of the formula I, substituents, such as, for example, the groups $R_1^a$, $R_1^b$ or $R_2$, can be converted into one another, or split off, within the scope laid down.

The reduction of the 3-cephem-1-oxide compounds to the 3-cephem compounds of the formula I can be carried out in a manner which is in itself known, by treatment with a reducing agents, if necessary in the presence of an activator. Possible reducing agents are catalytically activated hydrogen, using noble metal catalysts which contain palladium, platinum or rhodium; reducing tin, iron, copper or manganese cations which are used in the form of corresponding compounds or complexes of inorganic or organic type, for example as tin-II chloride or acetate, iron-II chloride, sulphate or oxalate, copper-I chloride, benzoate or oxide, or manganese-II chloride, sulphate, acetate or oxide, or as complexes, for example with ethylenediamine-tetraacetic acid or cyanotriacetic acid; reducing dithionite, iodide or ferrocyanide anions which are used in the form of corresponding inorganic or organic salts, such as alkali metal salts, for example sodium or potassium dithionite, sodium or potassium iodide or sodium or potassium ferrocyanide, or in the form of the corresponding acids, such as hydriodic acid; reducing trivalent inorganic or organic phosphorus compounds, such as phosphines, and also esters, amides and halides of phosphinous, phosphonous and phosphorous acid, as well as phosphorus-sulphur compounds corresponding to these phorphorus-oxygen compounds, such as, for example, triphenylphosphine, diphenylphosphinous acid methyl ester, benzenephosphonous acid dimethyl ester, phosphorous acid triphenyl ester, phosphorus trichloride and the like; reducing halogenosilane compounds which possess at least one hydrogen atom bonded to the silicon atom and which can also contain organic radicals in addition to the halogen, such as monochlorosilane, dichlorosilane or trichlorosilane, diphenylchlorosilane and the like; and reducing quaternary chloromethyleneiminium salts, especially chlorides or bromides, wherein the iminium group is substituted by a bivalent or two monovalent organic radicals such as optionally substituted lower alkylene or lower alkyl groups, such as N-chloromethylene-N,N-diethyliminium chloride.

As activators which are used together with those of the abovementioned reducing agents which do not themselves exhibit Lewis acid properties, that is to say which above all are employed together with the dithionite, iodide or ferrocyanide reducing agents and the non-halogen-containing trivalent phosphorus reducing agents, or which are employed in the catalytic reduction, there should in particular be mentioned organic carboxylic acid halides and sulphonic acid halides, and also sulphur, phosphorus or silicon halides having a second order hydrolysis constant equal to or greater than that of benzyl chloride, for example phosgene, oxalyl chloride, acetyl chloride, chloroacetyl chloride, p-toluenesulphonic acid chloride, methane-sulphonic acid chloride, thionyl chloride, phosphorus oxychloride, phosphorus trichloride, dimethylchlorosilane or trichlorosilane and also suitable acid anhydrides, such as trifluoroacetic anhydride, or cyclic sultones, such as ethanesultone, 1,3-propanesultone, 1,3-butanesultone or 1,3-hexanesultone.

The reduction is preferably carried out in the presence of solvents or mixtures thereof, the choice of which is above all determined by the solubility of the starting materials and the choice of the reducing agent, such as, for example, lower alkanecarboxylic acids or esters thereof, such as acetic acid and ethyl acetate, in the case of the catalytic reduction and, for example, optionally substituted, such as halogenated or nitrated, aliphatic, cycloaliphatic, aromatic or araliphatic hydrocarbons, for example benzene, methylene chloride, chloroform or nitromethane, suitable acid derivatives, such as lower alkanecarboxylic acid esters or nitriles, for example ethyl acetate or acetonitrile, or amides of inorganic or organic acids, for example dimethylformamide or hexamethylphosphoramide, ethers, for example diethyl ether, tetrahydrofurane or dioxane, ketones, for example acetone, or sulfoxides, especially aliphatic sulfoxides, for example dimethylsulfoxide or tetramethylenesulfoxide, and the like, in conjunction with the chemical reducing agents, these solvents preferably being anhydrous. The reaction is in these cases usually carried out at temperatures of about $-20°$ to about $100°$ C, but when using very reactive activators the reaction can be carried out at lower temperatures.

In the above variant of the isomerisation process, it is possible not only to oxidise the ring sulphur atom but also, simultaneously, the sulphur atom of the etherified mercaptomethyl group, and in the resulting 3-cephem compounds the latter can also be reduced simultaneously with the ring sulphoxide group.

In the 3-cephem compounds of the formula IV it is possible, within the scope which has been defined, to convert substituents into other substituents in a manner which is in itself known, for example as described above for the corresponding 2-cephem compounds.

The above compounds of the formula IV are known; those wherein $R_1{}^a$ represents an acyl radical occurring in pharmacologically active N-acyl derivatives of 6-amino-penam-3-carboxylic acid compounds or 7-amino-3-em-4-carboxylic acid compounds, $R_1{}^b$ represents hydrogen and $R_2$ represents hydrogen or a radical which can be replaced by hydrogen under physiological conditions, exhibit valuable pharmacological properties, especially against micro-organisms, such as Gram-positive and Gram-negative bacteria, for example *Staphylococcus aureus*, penicillin-resistant *Staphylococcus aureus* and *Escherichia coli*. Compounds of the formula IV can also be used as intermediate products for the manufacture of other compounds, especially of pharmacologically valuable compounds, for example those mentioned above.

The example which follows serves to illustrate the invention.

EXAMPLE 1:

50 g of methylmercaptan and 30 ml of trifluoroacetic acid are added to 15.0 g of 3-acetoxymethyl-7β-phenylacetylamino-2-cephem-4ξ-carboxylic acid in a pressure tube (Pyrex glass) whilst cooling in a solid carbon dioxide/acetone mixture. The glass tube is sealed and is allowed to warm to room temperature, with occasional shaking; the material dissolves completely. After a reaction time of 16 hours at room temperature, the glass tube is opened and after the methylmercaptan has escaped, the contents, with added toluene, are concentrated under a waterpump vacuum at 30° C bath temperature. The residue is caused to crystallise by squirting diethyl ether onto it. The crude product is filtered off and recrystallised from a mixture of methyl acetate and cyclohexane. This gives 3-methylthio-methyl-7β-phenylacetylamino-2-cephem-4ξ-carboxylic acid, which is pure according to thin layer chromatography, in the form of colourless crystals which are dried for 16 hours in a high vacuum at 30° C; melting point 162–166° C (with decomposition); thin layer chromatogram (silica gel): Rf = 0.60 (system: n-butanol/acetic acid/water, 75:75:21), Rf = 0.59 (system: n-butanol/ethanol/water, 40:10:50) and Rf = 0.53 (system: chloroform/methanol, 1:1); ultraviolet absorption spectrum (in 95% strength ethanol): $\lambda_{max}$ =235 mµ ($\epsilon$ = 7,900): infra-red absorption spectrum (in mineral oil): characteristic bands at 3.03µ, 5.65µ, 5.76µ, 6.00µ and 6.52µ.

EXAMPLE 2

A solution of 0.39 g of diphenyldiazomethane in 5 ml of petroleum ether is added dropwise over the course of half an hour to a solution of 0.5 g of 3-methylthiomethyl-7β-phenylacetylamino-2-cephem-4α-carboxylic acid in 20 ml of dioxane, while stirring. The solution is stirred for a further 15 hours at room temperature, treated with a few drops of glacial acid and concentrated under reduced pressure. The residue is recrystallised from methyl acetate and gives pure 3-methylthiomethyl-7β-phenylacetylamino-2-cephem-4α-carboxylic acid diphenylmethyl ester which is dried for 16 hours at room temperature in a high vacuum. Melting point 175–177° C; thin layer chromatogram (silica gel): Rf = 0.77 (system: chloroform/methanol, 1:1); Rf = 0.17 (system: toluene/acetone, 2:1); $[\alpha]_D^{20}$ +342° ± 1° (c = 1.011 in dioxane); ultraviolet absorption spectrum (in 95% strength aqueous ethanol): $\lambda_{max}$ = 255 mμ (ε = 7,800) and $\lambda_{min}$ = 244 mμ (ε = 7,200), infra-red absorption spectrum (in methylene chloride): characteristic bands at 2.92μ, 5.61μ, 5.73μ, 5.92μ, 6.25μ and 6.67μ.

EXAMPLE 3

A solution of 0.390 g of 3-acetoxymethyl-7β-phenylacetylamino-2-cephem-4α-carboxylic acid and 0.145g of 2-mercapto-5-methyl-1,3,4-thiadiazole in 5 ml of absolute trifluoroacetic acid is left to stand at room temperature for 2 hours. The clear solution is twice diluted with toluene and evaporated in a high vacuum. The residue is recrystallised from a mixture of methanol and ethyl acetate and is dried for 20 hours at room temperature in a high vacuum for producing an analytical sample. This gives 3-[(5-methyl-1,3,4-thiadiazol-2-yl)-thiomethyl]-7β-phenylacetylamino-2-cephem-4α-carboxylic acid, melting point = 155–159° C (with decomposition); thin layer chromatogram (silica gel): Rf = 0.46 (system: n-butanol/acetic acid/water, 75:7.5:21), Rf = 0.32 (system: n-butanol/ethanol/water, 40:10:50) and Rf = 0.27 (system: ethyl acetate/acetic acid, 9:1); $[\alpha]_D^{20}$ = + 198° (c = 0.750% in dioxane); ultraviolet absorption spectrum (in ethanol): $\lambda_{max}$ =258 mμ (ε = 11,300) and $\lambda_{min}$ = 238 mμ (ε = 9,300); infra-red absorption spectrum (in mineral oil): characteristic bands at 3.03μ, 5.68μ, 5.77μ, 6.02μ, 6.26μ and 6.57μ.

EXAMPLE 4

A mixture of 0.390 g of 3-acetoxymethyl-7β-phenylacetyl-amino-2-cephem-4α-carboxylic acid and 0.122 g of 5-mercapto-1-methyltetrazole in 5 ml of absolute trifluoroacetic acid is left to stand for 2 hours at room temperature and the reaction mixture is twice evaporated in a high vacuum, with addition of toluene in each case. The residue is crystallised from ethyl acetate; this gives 3-[(1-methyl-5-tetrazolyl)-thiomethyl]- 7β-phenylacetylamino-2-cephem-4α-carboxylic acid. An analytical sample is recrystallised from a mixture of methanol and ethyl acetate, melting point 114–115° C; thin layer chromatogram silica gel): Rf = 0.44 (system: n-butanol/acetic acid/water, 75: 7.5:21) and Rf = 0.32 (system: n-butanol/ethanol/water, 40:10:50); $[\alpha]_D^{20}$ = +205° ± 1° (c = 1.033 in dioxane); ultraviolet absorption spectrum (in ethanol): $\lambda_{max}$ = 254 mμ (9,600) and $\lambda_{min}$ = 244 mμ (ε = 9,100); infra-red absorption spectrum (in mineral oil): characteristic bands at 3.02μ, 5.67μ, 5.77μ, 6.02μ, 6.22μ and 6.53μ.

EXAMPLE 5

The following compounds can be prepared analogously: 7β[(2-tert.butoxycarbonylamino-2-phenylacetyl)-amino]-3- methylthiomethyl-2-cephem-4α-carboxylic acid; 7β-cyanoacetylamino-3-[(1-methyl-5-tetrazolyl)-thiomethyl]-2-cephem-4α-carboxylic acid; and 3-[(5-methyl-1,3,4-thiadiazol-2-yl)- thiomethyl]-7-[(1-tetrazolyl)-acetylamino]-2-cephem-4α-carboxylic acid.

EXAMPLE 6

The compounds mentioned in Examples 1–5 can be converted into the corresponding 3-cephem compounds in a manner which is in itself known, preferably with prior conversion to corresponding 4-carboxylic acid esters:

3-methylthiomethyl-7β-phenylacetylamino-2-cephem-4α-carboxylic acid diphenylmethyl ester ⟶ 3-methylthiomethyl- 7β-phenylacetylamino-3-cephem-4-carboxylic acid diphenylmethyl ester ⟶ 3-methylthiomethyl-7β-phenylacetylamino-3-cephem-4-carboxylic acid.

3-[(5-Methyl-1,3,4-thiadiazolyl)-thiomethyl]-7β-phenylacetylamino-2-cephem-4α-carboxylic acid ⟶ 3-[(5-methyl-1,3,4- thiadiazolyl)- thiomethyl]-7β-phenylacetylamino-2-cephem- 4α-carboxylic acid diphenylmethyl ester ⟶ 3-[(5-methyl-1,3,4- thiadiazolyl)- thiomethyl]-7β- phenylacetylamino-3-cephem-4-carboxylic acid diphenylmethyl ester⟶3-[(5-methyl-1,3,4-thiadiazolyl)- thiomethyl]-7β-phenylacetylamino-3-cephem-4-carboxylic acid.

3-[(1-Methyl-5-tetrazolyl)-thiomethyl]-7β-phenylacetyl-amino-2-cephem-4α-carboxylic acid ⟶ 3-[(1-methyl-5-tetrazolyl)- thiomethyl]-7β-phenylacetylamino-2-cephem-4α-carboxylic acid deiphenylmethyl ester ⟶ 3-[(1-methyl-5-tetrazolyl)-thiomethyl]-7β-phenylacetylamino-3-cephem-4-carboxylic acid diphenylmethyl ester ⟶ 3-[(1-methyl-5-tetrazolyl)-thiomethyl]- 7β-phenylacetylamino-3-cephem-4-carboxylic acid.

7β-[(2-tert.-Butoxycarbonylamino-2-phenylacetyl)-amino]- 3-methylthiomethyl-2-cephem-4β-carboxylic acid⟶7β-[(2- tert.-butoxycarbonylamino-2-phenylacetyl)amino]-3-methylthiomethyl- 2-cephem-4β-carboxylic acid diphenylmethyl ester ⟶ 7β-[(2-tert.-butoxycarbonylamino-2-phenylacetyl)-amino]- 3-methylthiomethyl-3-cephem-4-carboxylic acid diphenylmethyl ester⟶7β-[(2-amino-2-phenylacetyl)-amino]-3-methylthiomethyl- 3-cephem-4-carboxylic acid, for example in the form of the inner salt.

7β-Cyanoacetylamino-3-[(1-methyl-5-tetrazolyl)-thiomethyl]- 2-cephem-4β-carboxylic acid⟶7β-cyanoacetylamino-3- [(1-methyl-5-tetrazolyl)- thiomethyl]-2-cephem-4β-carboxylic acid diphenylmethyl ester⟶7β-cyanoacetylamino-3-[(1- methyl-5-tetrazolyl)- thiomethyl]-3-cephem-4-carboxylic acid diphenylmethyl ester ⟶ 7β-cyanoacetylamino-3-[(1-methyl-5- tetrazolyl)-thiomethyl]-3-cephem-4-carboxylic acid.

3-[(5-Methyl-1,3,4-thiadiazol-2-yl)-thiomethyl]-7-[(1-tetrazoolyl)-acetylamino]-2-cephem-4β-carboxylic acid ⟶ 3- [(5-methyl-1,3,4-thiadiazol-2-yl)-thiomethyl]-7-[(1- tetrazolyl)-acetylamino]-2-cephem-4β-carboxylic acid diphenylmethyl ester ⟶ 3-[(5-methyl-1,3,4-thiadiazol-2-yl)-thiomethyl]-7-[(1- tetrazolyl)-acetylamino]-3-cephem-4-carboxylic acid diphenylmethyl ester ⟶ 3-[(5-methyl-1,3,4-thiadiazol-2- yl)-thiomethyl]-7-[(1-tetrazolyl)-acetylamino]-3-cephem-4-carboxylic acid.

We claim:

1. Process for the manufacture of a member selected from the group consisting of 7-N-$R_1^a$-N-$R_1^b$-amino-3-R-thiomethyl-2-cephem-4 carboxylic acid compounds of the formula

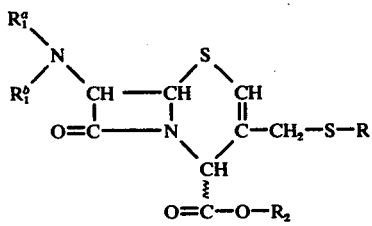

wherein R represents methyl, thiadiazolyl, tetrazolyl, methyl-substituted thiadiazolyl, or methyl-substituted tetrazolyl, $R_1^b$ is hydrogen, $R_1^a$ represents hydrogen, cyanoacetyl or an acyl radical of the formula

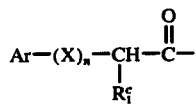

wherein Ar is phenyl or tetrazolyl, X is oxygen, $n$ denoted 0 or 1 and $R_1^c$ denotes hydrogen or, if $n$ represents 0, denotes α-poly-branched lower alkoxycarbonylamino, phenyl-lower alkoxycarbonylamino or phenyl-lower alkoxycarbonylamino substituted by lower alkoxy, nitro, or hydroxyl, α-poly-branched lower alkoxycarbonyloxy, 2-halogeno-lower alkoxycarbonyloxy, or formyloxy, or represents a 5-amino-5-carboxyvaleryl radical, wherein the amino and/or carboxyl group are optionally present, as lower alkanoylamino, dichloro-acetylamino, or phthaloylamino, or as phenyl-lower alkoxy-carbonyl, and $R_2$ denotes hydrogen, lower alkyl, α-poly-branched lower alkyl, or 2 halogeno-lower alkyl, nitrobenzyl, diphenylmethyl or lower alkoxy-substituted diphenylmethyl, and salts of such compounds with alkali and alkaline earth metals, ammonia or organic amines, if $R_2$ represents hydrogen, or with inorganic acids or organic sulfonic acids, if $R_1^a$ and $R_1^b$ both represent hydrogen or inner salts of such compounds, if $R_2$, $R_1^a$ and $R_1^b$ all represent hydrogen, wherein a 7-(N-$R_1^A$-N-$R_1^b$-amino)-3-Y-methyl-2-cephem-4-carboxylic acid compound of the formula

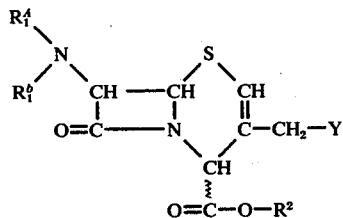

wherein $R_1^b$ and $R_2$ have the above-mentioned meanings, $R_1^A$ represents trityl, tri-lower alkyl silyl, phenylglycyl, phenylacetyl or phenoxyacetyl, and Y represents hydroxy, lower alkanoyloxy or halogeno acetoxy, is reacted with a compound of the formula R-SH (III), in the presence of trifluoroacetic acid with the proviso that when Y represents trifluoroacetoxy, the reaction can be carried out in the absence of trifluoroacetic acid.

2. Process according to claim 1, wherein an esterified hydroxyl group Y represents a member selected from the group consisting of a lower alkanoyloxy and a halogeno acetoxy group.

3. Process according to claim 2, wherein an esterified hydroxylgroup Y represents a member selected from the group consisting of acetyloxy and trifluoroacetyloxy.

4. Process according to claim 1, wherein a starting material of the formula II, wherein Y represents trifluoroacetoxy is reacted with a compound of the formula III.

5. Process according to claim 1, wherein a starting material of the formula II, wherein Y represents a member selected from the group consisting of a free hydroxyl group and a hydroxyl group esterified by a lower alkane-carboxylic acid or a halogeno acetic acid, is reacted with a compound of the formula III in the presence of trifluoroacetic acid.

* * * * *